(12) United States Patent
Tamura et al.

(10) Patent No.: US 6,639,381 B2
(45) Date of Patent: Oct. 28, 2003

(54) DEFIBRILLATOR WITH REPLACEABLE AND RECHARGEABLE POWER PACKS

(75) Inventors: Paul S. Tamura, Seattle, WA (US); Stephen B. Johnson, Clinton, WA (US); Richard C. Nova, Kirkland, WA (US); Joseph L. Sullivan, Kirkland, WA (US)

(73) Assignee: Medtronic Physio-Control Corp., Redmond, WA (US)

( * ) Notice: Subject to any disclaimer, the term of this patent is extended or adjusted under 35 U.S.C. 154(b) by 45 days.

(21) Appl. No.: 10/035,297

(22) Filed: Oct. 26, 2001

(65) Prior Publication Data

US 2003/0080712 A1 May 1, 2003

(51) Int. Cl.$^7$ ............................................... H01M 10/46
(52) U.S. Cl. ......................................................... 320/103
(58) Field of Search ................................. 320/103, 107, 320/112, 132, 166; 607/33, 34, 35, 36, 29

(56) References Cited

U.S. PATENT DOCUMENTS

| | | | |
|---|---|---|---|
| 5,314,451 A | * | 5/1994 | Mulier |
| 5,620,465 A | | 4/1997 | Olson et al. |
| 5,741,305 A | | 4/1998 | Vincent et al. |
| 5,998,052 A | | 12/1999 | Yamin |
| 6,038,473 A | | 3/2000 | Olson et al. |
| 6,154,007 A | | 11/2000 | Shaver et al. |
| 6,157,531 A | | 12/2000 | Breyen et al. |
| 6,249,105 B1 | | 6/2001 | Andrews et al. |
| 6,268,709 B1 | * | 7/2001 | Lee et al. |
| 6,288,518 B1 | * | 9/2001 | Yang et al. |
| 2002/0138103 A1 | | 9/2002 | Mulhauser et al. |

FOREIGN PATENT DOCUMENTS

| | | |
|---|---|---|
| EP | 0 757 912 A2 | 2/1997 |
| EP | 1 093 829 A1 | 4/2001 |
| WO | WO 96/22811 | 8/1996 |

OTHER PUBLICATIONS

Yamin et al., "High Energy and Power Densities Pulse Plus™ Battery," Tadiran Batteries Ltd., P.O. Box 1 K. Ekron, 70500 Israel, 1999. No date.
"Publicaion: Advances in R&D for the Commercialization of Small Fuel Cells," http://www.knowledgefoundation.com/sfcbook.html, 1999. No date.
"Tadiran HLC (Hybrid Layer Capacitor) Model HLC–1550," Tadiran Batteries Ltd., PulsesPlus™, Sep., 2000.
"Lithium Battery TL–6955/S," Tadiran Batteries Ltd., Oct. 2000.
"Technical Presentation to Medtronic Physio–Control Overview," Tadiran Batteries Ltd., PulsesPlus™, Nov., 2000.
"Pulses Plus Battery System for High Energy High Power Applications," The $17^{th}$ International Seminar and Exhibit on Primary & Secondary Batteries, Mar., 2000.
"Safety and Environmental Tests," National Marketing Meeting, Rehovot, Dec., 1999. No date.
Yamin et al., "Pulses Plus Battery System for High Energy High Power Applications," The $19^{th}$ International Seminar on Primary and Secondary Batteries, Fort Lauderdale, Florida, Mar., 2000.

* cited by examiner

*Primary Examiner*—Edward H. Tso
(74) *Attorney, Agent, or Firm*—Shumaker & Sieffert, P.A.

(57) ABSTRACT

The power source in a portable defibrillator includes a replaceable first power pack and a rechargeable second power pack. The first power pack charges the second power pack. The second power pack supplies most of the energy needed to administer a defibrillation shock. The first power pack may include one or more lithium thionyl chloride batteries. The second power pack may include one or more lithium ion batteries and/or ultracapacitors.

17 Claims, 5 Drawing Sheets

DEFIBRILLATOR WITH REPLACEABLE AND RECHARGEABLE POWER PACKS

TECHNICAL FIELD

The invention relates to medical devices, and in particular, to power sources for portable defibrillators.

BACKGROUND

Cardiac arrest and ventricular fibrillation are life-threatening medical conditions that may be treated with external defibrillation. External defibrillation includes applying electrodes to the patient's chest and delivering an electric shock to the patient to depolarize the patient's heart and restore normal sinus rhythm. The chances that a patient's heart can be successfully defibrillated increase significantly if a defibrillation shock is applied quickly. In many cases, it is more expedient to bring a defibrillator to the patient than to bring the patient to a defibrillator.

Many external defibrillators are portable. Portable external defibrillators may be used in hospitals and outside hospital settings as well. Paramedics, emergency medical technicians and police officers, for example, may carry portable external defibrillators in their vehicles. In addition, automated external defibrillators (AED's) may be available in public venues such as airports, health clubs and auditoriums. Portable external defibrillators are compact and lightweight.

Before an external defibrillator is used to administer a shock, the energy to be delivered to the patient must be stored in an energy storage device, such as a capacitor. Many defibrillators use a charging circuit to transfer energy from a power source, such as an electrical outlet or a battery, to the energy storage device. When a switch is closed, the energy storage device delivers at least a part of the stored energy from electrode to electrode through the patient's chest. Delivery of energy from the energy storage device is completed in a few milliseconds.

Following administration of one shock, it may be necessary to administer another. The charging circuit draws energy from the power source and transfers the energy to the energy storage device. When the energy storage device is sufficiently charged, another shock may be administered. In order to charge the energy storage device quickly, the power source may be called upon to supply approximately fifty to one hundred fifty watts of power. The power supplied is a function of the voltage of the power source and the current supplied by the power source. To supply fifty to one hundred fifty watts, a ten-volt power source, for example, may be called upon to supply between five to fifteen amperes of current.

Some conventional external defibrillators are powered by a connection to an electrical outlet. These "line-powered" defibrillators carry risks of injury to the patient, to bystanders and to persons operating the defibrillator. In particular, a line-powered defibrillator carries a risk of sending line power to the patient and a risk of sending high voltage to the power cord during delivery of the defibrillation shock. Accordingly, a line-powered defibrillator usually includes electrical isolation circuitry to prevent the line power from reaching the patient and to prevent the defibrillation energy from passing through the power cord. Some isolation circuitry, such as a transformer, is large and heavy, adversely affecting the portability of the external defibrillator. In addition, a line-powered defibrillator cannot draw energy from an electrical outlet when the patient is far from an electrical outlet.

Other external defibrillators use one or more batteries as a power source. A battery-powered defibrillator does not require a power cord and therefore does not require the bulky isolation circuitry needed for a power cord. In conventional external defibrillators, batteries may be permanently mounted or replaceable.

When a defibrillator includes batteries that are permanently mounted in the device, the batteries usually are rechargeable. Many rechargeable batteries, such as nickel-cadmium batteries, sealed lead acid batteries or nickel-metal-hydride batteries, require a special recharging apparatus. The addition of recharging apparatus to the defibrillator adds to the bulk, weight and cost of the device. In addition, the recharging apparatus may be line-powered, which in turn necessitates electrical isolation circuitry for safety.

A further drawback to rechargeable batteries is short shelf life. Nickel-metal-hydride batteries, for example, discharge within a few months, even when no load is applied. Some rechargeable batteries, such as nickel-cadmium batteries, need to undergo conditioning cycles periodically to deliver optimum performance.

External defibrillators may include capacitors to smooth the power supplied by the rechargeable batteries. Although capacitors can be used as a rechargeable source of dc power, banks of conventional capacitors are incapable of supplanting the rechargeable batteries as a power source. Banks of conventional capacitors store too little energy, or are too bulky for a portable external defibrillator, or both.

As an alternative to permanent rechargeable batteries, a defibrillator may use replaceable batteries as a power source. Many replaceable batteries are not capable of delivering the energy demanded by the charging circuit. Replaceable batteries that can deliver the energy typically require heavy duty, low impedance connectors to carry the high currents safely, and the bulky connectors add to the weight and cost of the device. Heavy duty, low impedance conductors also increase the risk of inadvertent shock to an operator, because of the comparatively large size of the conductors.

In addition, some replaceable high capacity batteries pose additional hazards. When lithium sulfur dioxide batteries fail, for example, the batteries vent noxious gases, and when lithium manganese batteries fail, the batteries vent flammable electrolytes.

SUMMARY

In general, the invention uses a power source that includes a first power pack and a second power pack for use in supplying energy to the energy storage device of a defibrillator. The first power pack is replaceable and the second power pack is rechargeable. The replaceable first power pack is used to charge the rechargeable second power pack. The replaceable first power pack may also be used to maintain the charge of the second power pack. When a charging circuit draws energy from the power source to charge an energy storage device associated with the defibrillator, the charging circuit draws the energy principally from the rechargeable second power pack.

The replaceable first power pack and rechargeable second power pack cooperate to provide the energy needed by the charging circuit to charge the energy storage device. In one exemplary embodiment, the replaceable first power pack comprises batteries, rendering unnecessary the electrical isolation circuitry that would be present in a line-powered defibrillator.

Furthermore, the first power pack recharges the second power pack without the need for a special charging device.

In a typical implementation, the first power pack charges the second power pack via a parallel electrical connection. Because no special charging device is needed, the power source is smaller and lighter, and the defibrillator is more portable.

The first power pack may include one or more lithium thionyl chloride ($Li/SOCl_2$) batteries. In one exemplary embodiment, the first power pack includes three lithium thionyl chloride batteries.

The second power pack may include one or more lithium ion batteries. In one exemplary embodiment, the second power pack includes six lithium ion batteries, with three pairs of lithium ion batteries coupled in parallel.

Lithium thionyl chloride batteries and lithium ion batteries work well together. The batteries can be selected to have matched working voltages and can operate over a wide temperature range. Both kinds of batteries are small and light, and help make the defibrillator small, light and portable. Working together, the batteries have a very long shelf life and can supply energy even if the defibrillator has been idle for an extended period. In addition, neither battery vents harmful electrolytes in case of failure.

A replaceable first power pack such as a lithium thionyl chloride battery may have a low power output and may be unable supply high amperages. In that case, heavy duty, low impedance connectors are not needed to couple the first power pack to the second power pack. Because of its low power output, the first power pack cannot supply the current demanded by the charging circuit. The first power pack can, however, charge a second power pack, such as a lithium ion battery, at a comparatively slow rate.

The second power pack may include one or more capacitors. Like rechargeable batteries, capacitors can be charged, used as a direct-current power source, and recharged. In one exemplary embodiment, the second power pack includes ultracapacitors, which are compact capacitors with high energy density. The ultracapacitors may be grouped into one or more banks of ultracapacitors, with the banks of ultracapacitors coupled in parallel with the replaceable first power pack. The second power pack may include both batteries and capacitors.

The second power pack generally has a much higher power output than the first power pack. The second power pack can therefore supply the current demanded by the charging circuit to charge the energy storage device quickly. The high-current connectors that conduct that current are shielded from the operator inside the case of the defibrillator.

In one embodiment, the invention is directed to a defibrillator that includes a replaceable first battery coupled to a rechargeable second battery. The first battery may comprise a lithium thionyl chloride battery and the second battery may comprise a lithium ion battery. The second battery may be permanently mounted inside the defibrillator. In ordinary use, the replaceable first battery and the rechargeable second battery may be coupled in parallel.

In another embodiment, the invention is directed to a device comprising a power source that supplies energy to an energy storage device in a defibrillator. The power source comprises a replaceable first power pack coupled to a rechargeable second power pack. Furthermore, the replaceable first power pack comprises at least one lithium thionyl chloride battery and the rechargeable second power pack comprises at least one lithium ion battery.

In an additional embodiment, the invention is directed to a defibrillator that includes a replaceable first power pack coupled to a rechargeable second power pack. The second power pack includes a rechargeable battery, a capacitor, or both, and stores at least 100 joules. The second power pack may include one or more ultracapacitors.

In a further embodiment, the invention is directed to a method comprising charging a second power pack with a replaceable first power pack in parallel with the second power pack, charging an energy storage device with energy from the second power pack and delivering energy from the energy storage device to a defibrillation electrode. Charging the second power pack may include, for example, charging a rechargeable battery or an ultracapacitor in the second power pack.

In an added embodiment, the invention is directed to a method comprising uncoupling a first power pack from a rechargeable second power pack in a defibrillator and coupling a fresh first power pack to the rechargeable second power pack. This method may also include replacing the electrodes on the defibrillator.

As noted above, the replaceable first power pack and rechargeable second power pack eliminate the need for some electrical isolation circuitry, special charging apparatus and heavy-duty connectors. Each of these advantages contributes to making the defibrillator portable and safe. In addition, lithium thionyl chloride batteries and lithium ion batteries are small, light and vent no harmful substances, further contributing to safety and portability. The batteries also have a long shelf life, can have matched working voltages and operate well over a wide temperature range.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
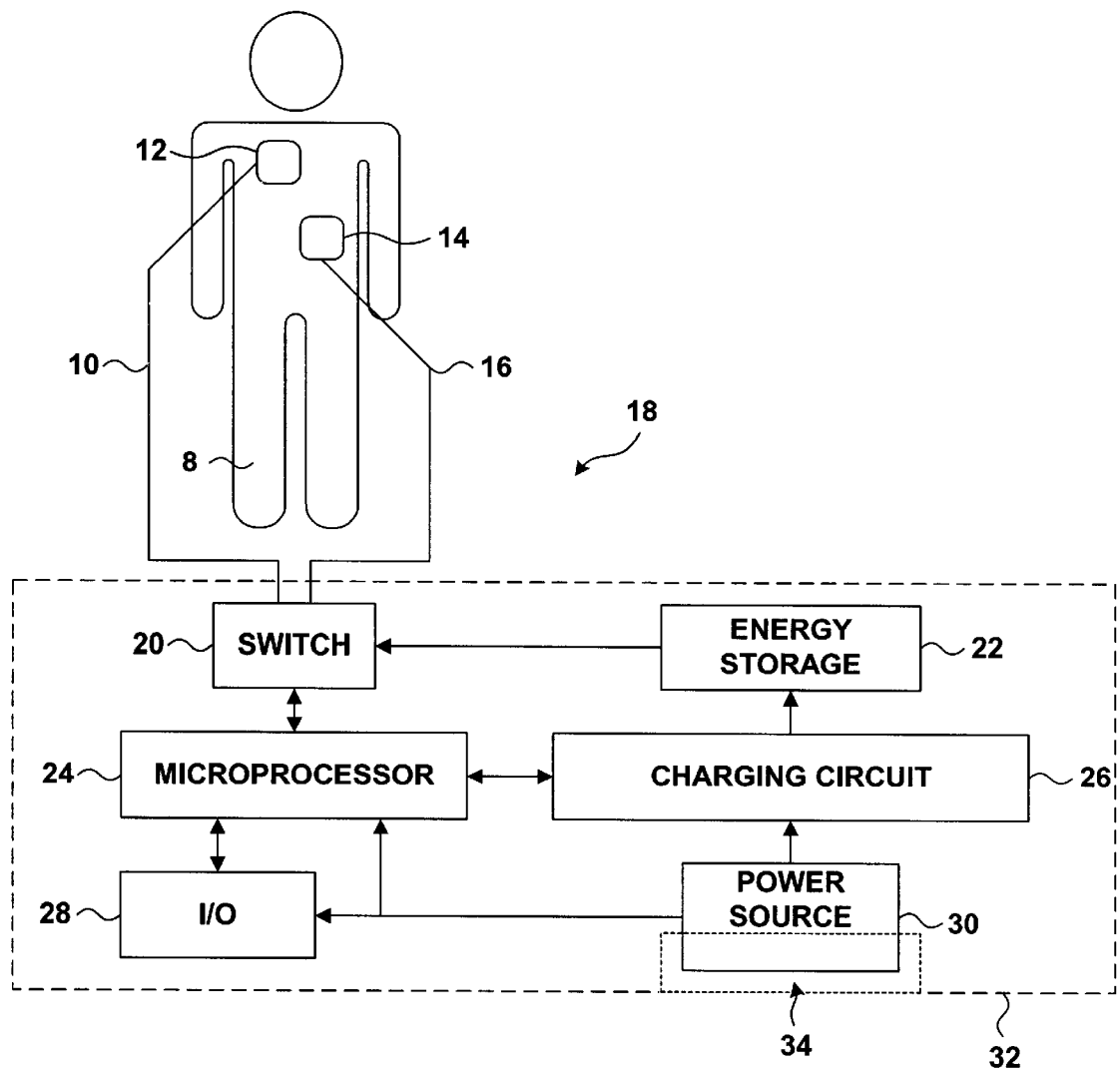
FIG. 1 is a block diagram illustrating an external defibrillator.

FIG. 1 is a block diagram showing a patient 8 coupled to an external defibrillator 18. Defibrillator 18 administers defibrillation therapy to patient 8 via electrodes 12 and 14, which may be hand-held electrode paddles or adhesive electrode pads placed on the skin of patient 8. The body of patient 8 provides an electrical path between electrodes 12 and 14.

Electrodes 12 and 14 are coupled to switch 20 via conductors 10 and 16. Usually electrodes 12 and 14 are replaceable. Switch 20 couples electrodes 12 and 14 to the output of an energy storage device 22. Switch 20 is of conventional design and may be formed, for example, of electrically operated relays. Alternatively, switch 20 may comprise an arrangement of solid-state devices such as silicon-controlled rectifiers or insulated gate bipolar transistors. In each case, switch 20 is capable of carrying relatively high currents from energy storage device 22 to electrodes 12, 14.

Energy storage device 22 includes components, such one or more capacitors, that store the energy to be delivered to patient 8 via electrodes 12, 14. Before a defibrillation pulse may be delivered to patient 8, energy storage device 22 must be charged. A microprocessor 24 directs a charging circuit 26 to charge energy storage device 22 to a high voltage level. Charging circuit 26 comprises, for example, a flyback charger that transfers energy from a power source 30 to energy storage device 22. Because the life of patient 8 may depend upon receiving defibrillation, charging should take place rapidly so that the defibrillation shock may be delivered with little delay.

When the energy stored in energy storage device 22 reaches the desired level, defibrillator 18 is ready to deliver the defibrillation shock. The shock may be delivered automatically or manually. When the shock is delivered automatically, microprocessor 24 activates an input/output (I/O) device 28, such as an indicator light or a voice prompt, that warns the operator that defibrillator 18 is ready to deliver a defibrillation shock to patient 8. The warning informs the operator of the impending shock so that no one other than patient 8 will receive the defibrillation shock. Microprocessor 24 then activates switch 20 to electrically connect energy storage device 22 to electrodes 12 and 14, and thereby deliver a defibrillation shock to patient 8. In the case of a manual delivery, microprocessor 24 may activate an input/output (I/O) device 28 that informs the operator that defibrillator 18 is ready to deliver a defibrillation shock to patient 8. The operator may activate switch 20 and thereby deliver a defibrillation shock to patient 8.

Microprocessor 24 may perform other functions as well, such as monitoring electrocardiogram signals sensed via electrodes 12 and 14. Microprocessor 24 may determine whether patient 8 suffers from a condition that requires a defibrillation shock, and may also evaluate the efficacy of administered defibrillation shocks.

The goal of defibrillation is to depolarize the heart with electrical current and cause the heart to reestablish a normal sinus rhythm. In some patients, one shock is insufficient to reestablish normal rhythm, and one or more additional defibrillation shocks may be required. Before another shock may be administered, however, charging circuit 26 ordinarily must transfer energy from power source 30 to energy storage device 22, thereby recharging energy storage device 22. In recharging energy storage device 22, as in the initial charging, time is of the essence, and charging circuit 26 therefore charges energy storage device 22 quickly. In a typical implementation, charging circuit 26 may draw fifty to one hundred fifty watts from power source 30 to charge energy storage device 22. Power source 30 must therefore be capable of high power output and, consequently, high current output. Charging circuit 26 may draw, for example, one to twelve amperes from power source 30.

In the embodiment shown in FIG. 1, power source 30 comprises batteries and/or capacitors, and defibrillator 18 requires no electrical connection to an exterior power source such as an electrical outlet. Accordingly, defibrillator 18 does not have the drawbacks associated with a line-powered defibrillator. In particular, defibrillator 18 does not require cumbersome electrical isolation circuitry, and defibrillator 18 may be used at locations where no electrical outlet is present.

As will be described in more detail in connection with FIG. 2, power source 30 comprises a replaceable first power pack 40 coupled to a rechargeable second power pack 42. As will be illustrated in FIGS. 3 and 4, first power pack 40 may comprise one or more replaceable batteries. Second power pack 42 may comprise one or more rechargeable batteries, and/or one or more capacitors. Like rechargeable batteries, capacitors can be charged, used as a direct-current power source, and recharged. As used herein, "battery" comprises any device that stores electrical energy electrochemically. "Battery" may include, for example, an arrangement of one or more conventional electrochemical cells or fuel cells. "Capacitor" comprises any device that stores electrical energy in an electric field. Batteries and capacitors, independently and in cooperation, can be direct-current power sources.

Although power source 30 is located within defibrillator case 32, first power pack 40 may be removed from defibrillator 18 by removing first power pack 40 from compartment 34. In one embodiment of the invention, second power pack 42 is mounted permanently inside defibrillator case 32 and cannot be accessed via compartment 34.

In addition to supplying energy to charging circuit 26 and energy storage device 22, power source 30 also supplies power to microprocessor 24 and I/O device 28, e.g., via a power supply circuit (not shown in FIG. 1). When defibrillator 18 is not in use, microprocessor 24 and I/O device 28 use little or no power.

Figure 2:
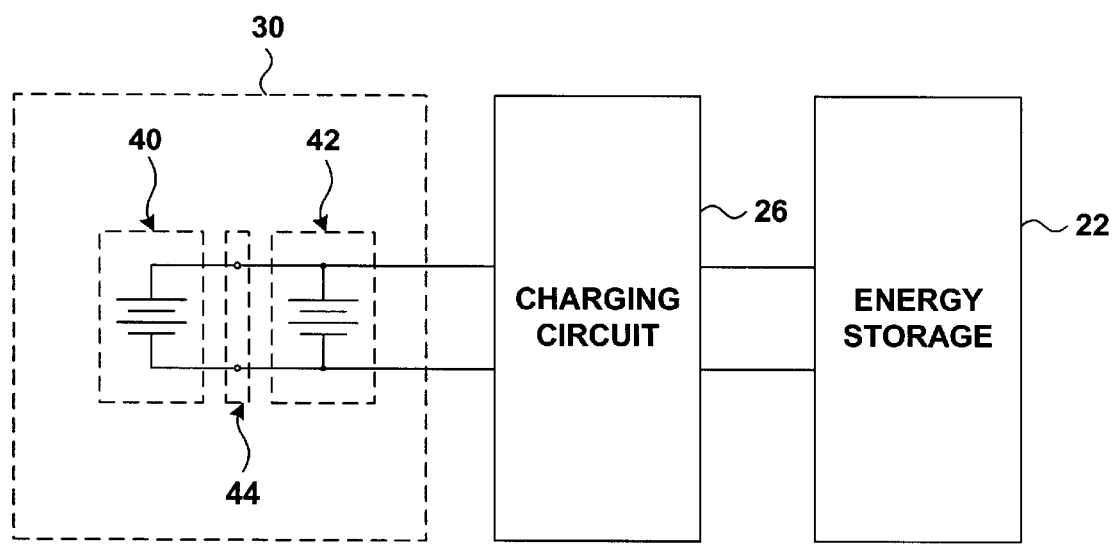
FIG. 2 is a circuit diagram of a power source in cooperation with a charging circuit and an energy storage device.

FIG. 2 is a circuit diagram showing power source 30 with charging circuit 26 and energy storage device 22. Power source 30 includes first power pack 40, which is replaceable, and second power pack 42, which is mounted inside case 32 of defibrillator 18 and which is ordinarily not replaceable. Second power pack 42 is rechargeable.

First power pack 40 is coupled in parallel to second power pack 42 by connection 44. The parallel connection causes first power pack 40 to hold second power pack 42 at the same voltage as first power pack 40. In addition, when the open circuit voltage of second power pack 42 is below the open circuit voltage of first power pack 40, first power pack 40 recharges second power pack 42 until the voltage across second power pack 42 is the same as the voltage across first power pack 40. As will be discussed below, with proper selection of first power pack 40 and second power pack 42, recharging may take place without a specialized recharger.

Figure 3:
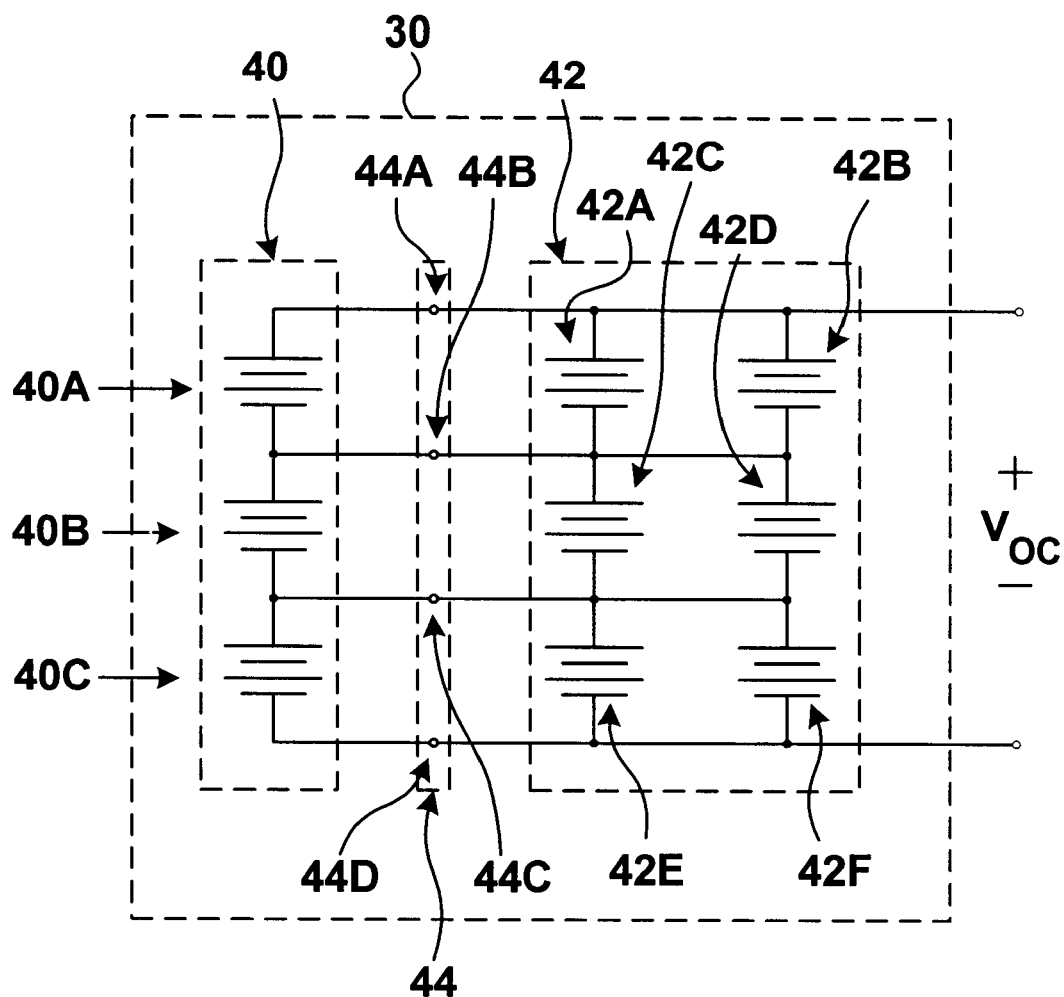
FIG. 3 is a circuit diagram of a power source illustrating an exemplary embodiment of the invention.

FIG. 3 is a circuit diagram showing an exemplary embodiment of the invention. Power source 30 comprises first power pack 40 and second power pack 42. In the embodiment shown in FIG. 3, first power pack 40 and second power pack 42 each include a plurality of batteries. First power pack 40 includes replaceable first batteries 40A, 40B and 40C, and second power pack 42 includes rechargeable second batteries 42A, 42B, 42C, 42D, 42E and 42F.

Replaceable batteries 40A, 40B and 40C may be packaged as a single unit, thereby making installation in compartment 34 easier. The cathode of battery 40B is coupled to the anode of battery 40A, and the anode of battery 40B is coupled to the cathode of battery 40C.

When first power pack 40 is coupled to second power pack 42 via connection 44, replaceable batteries and rechargeable batteries are placed in parallel. For example, replaceable battery 40A is coupled in parallel by connections 44A and 44B with rechargeable batteries 42A and 42B. Battery 40A therefore charges batteries 42A and 42B and/or holds batteries 42A and 42B to the open-circuit voltage of battery 40A.

In similar fashion, connectors 44B and 44C couple battery 40B in parallel with batteries 42C and 42D. Connectors 44C and 44D couple battery 40C in parallel with batteries 42E and 42F.

Power source 30 may comprise one or more resettable fuses (not shown in FIG. 3). The fuses may be in line with a connection that couples the cathode of a replaceable battery to the cathode of a rechargeable battery. In case the connection becomes shorted, the fuse prevents rapid discharging. Power source 30 may also comprise diodes (not shown in FIG. 3) across each battery. In case the battery failed, the diode would allow the current to bypass the failed battery.

In one embodiment of the invention, batteries 40A, 40B and 40C are lithium thionyl chloride batteries, such as lithium thionyl chloride batteries commercially available from Tadiran Batteries Ltd. of Israel. The nominal open circuit voltage of each lithium thionyl chloride battery is approximately 3.9 volts. When batteries 40A through 40C are coupled to batteries 42A through 42F as shown in FIG. 3, power necks 40 and 42 produce an open circuit voltage $V_{OC}$ of approximately 11.7 volts.

Lithium thionyl chloride batteries are small, yet store substantial energy. A typical lithium thionyl chloride battery, sized smaller than a "AA" battery, has a nominal discharge capacity of about 1.40 ampere-hours, which is approximately equivalent to the nominal discharge capacity of three "C" nickel-cadmium batteries. Nevertheless, lithium thionyl chloride batteries have very low power output, producing a maximum of about 10 milliamperes of current under ordinary operating conditions.

In addition, lithium thionyl chloride batteries have a very low self-discharge rate, giving them an exceptional shelf life. Lithium thionyl chloride batteries can stand unused for several years without undergoing significant discharge. Batteries having a long shelf life are advantageous, because they can power defibrillator 18 even when defibrillator 18 has sat idle for many months.

By themselves, however, lithium thionyl chloride batteries are insufficient to supply energy to defibrillator 18 because lithium thionyl chloride batteries cannot supply the heavy currents, and consequently cannot supply the power, needed to quickly recharge energy storage device 22. Charging circuit 26 may demand, for example, one to twelve amperes, and lithium thionyl chloride batteries cannot supply that magnitude of current.

The low current output of lithium thionyl chloride batteries, however, has advantages. Because lithium thionyl chloride batteries cannot produce large currents, the batteries are unlikely to overheat. Furthermore, connections 44A through 44D need not be constructed to conduct large currents. In other words, connection 44 need not comprise heavy duty, low impedance connectors. Accordingly, connections 44A through 44D are comparatively small and need not be heavily insulated. In one embodiment, for example, first power pack 40 may comprise a modular connector such as 70AA modular contacts commercially available from Bourns, Inc., which engages contacts in defibrillator case 32. In addition to saving cost and weight, the small size of connection 44 reduces the risk of an inadvertent contact by an operator.

Batteries 42A through 42F comprise rechargeable batteries, such as lithium ion rechargeable batteries. Lithium ion rechargeable batteries are also commercially available from Tadiran Batteries Ltd. of Israel. Unlike lithium thionyl chloride batteries, lithium ion rechargeable batteries are capable of delivering the high amperages demanded by charging circuit 26 to charge energy storage device 22 quickly. Low-impedance connections between batteries 42A through 42F and charging circuit 26 are completely enclosed in defibrillator case 32, and present no exposed connections or risk of inadvertent shock to an operator.

Lithium thionyl chloride batteries and lithium ion batteries cooperate well. Like lithium thionyl chloride batteries, lithium ion batteries can hold considerable energy, and yet are compact. When lithium thionyl chloride batteries and lithium ion batteries are used, first power pack 40 and second power pack 42 are small and light, enhancing the portability of defibrillator 18.

In addition, lithium thionyl chloride batteries and lithium ion batteries are also readily matched to each other, with both batteries having nearly identical working voltages. In other words, a lithium thionyl chloride battery may charge one or more lithium ion batteries to the lithium ion batteries' fully charged capacity, and hold the lithium ion batteries at that voltage.

Furthermore, the long shelf life of lithium thionyl chloride batteries helps hold the charge of lithium ion batteries for years. In this way, when defibrillator 18 is activated after many months sitting idle, lithium ion batteries will be able to supply the energy demanded by charging circuit 26.

When charging circuit 26 draws energy from rechargeable batteries 42A through 42F, batteries 42A through 42F undergo discharge. Because it may be necessary to recharge energy storage device 22 several times, second power pack 42 should not discharge too quickly. Second power pack 42 includes six batteries 42A through 42F, arranged in three sets of batteries coupled in parallel. These six batteries can typically supply enough current to recharge energy storage device 22 about twenty times or more before batteries 42A through 42F themselves require recharging. Defibrillator 18 may include an I/O device 28, such as an LED indicator, that indicates when energy in second power pack 42 is low.

Figure 4:
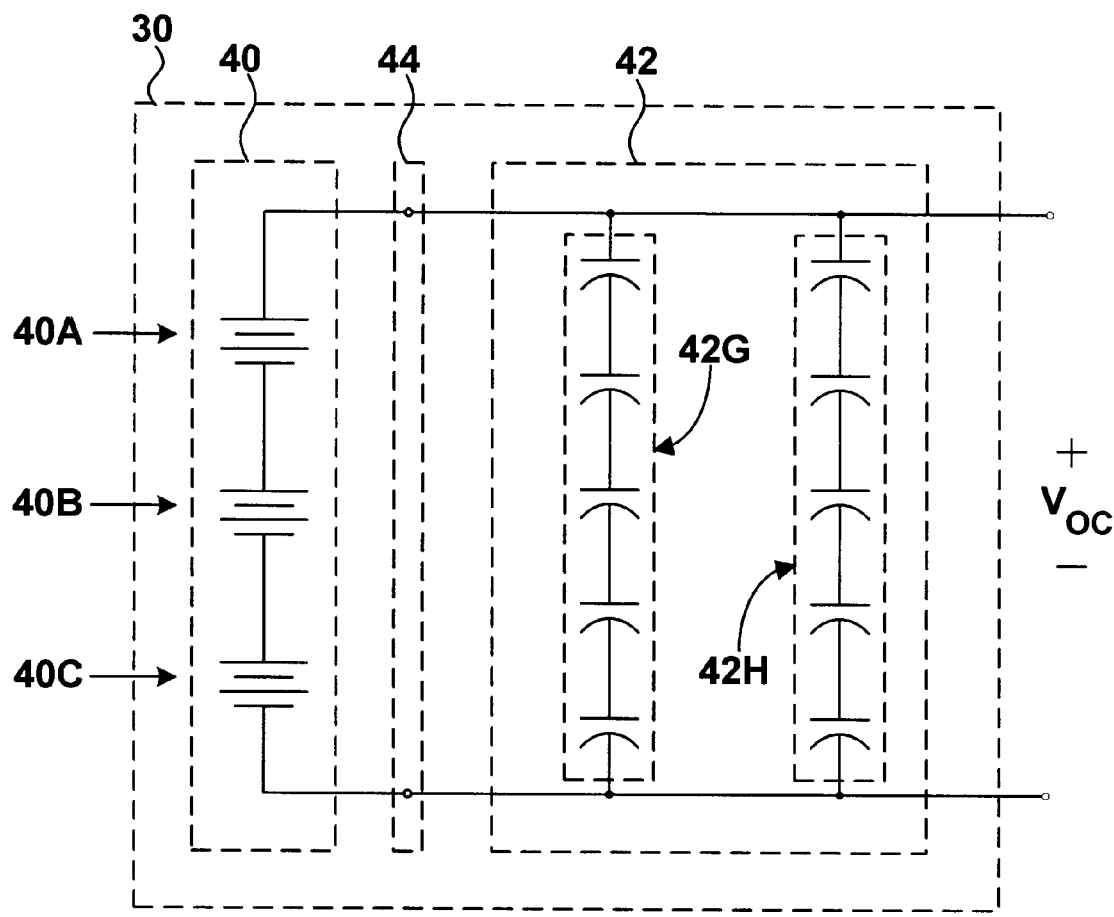
FIG. 4 is a circuit diagram of a power source illustrating another exemplary embodiment of the invention.

FIG. 4 is a circuit diagram showing another exemplary embodiment of the invention. Like the embodiment shown in FIG. 3, first power pack 40 includes a plurality of batteries. Second power pack 42 includes rechargeable banks of capacitors 42G, 42H. Each bank of capacitors 42G, 42H includes five capacitors in series. When first power pack 40 is coupled to second power pack 42 via connection 44, replaceable batteries in first power pack 40 charge the capacitors in second power pack 42.

Replaceable batteries 40A, 40B and 40C are coupled in parallel with capacitor banks 42G and 42H. As a result, batteries 40A, 40B and 40C charge capacitor banks 42G and 42H and/or hold capacitor banks 42G and 42H to the open-circuit voltage of batteries 40A, 40B and 40C.

Batteries 40A, 40B and 40C may be lithium thionyl chloride batteries, for example, producing an open circuit voltage $V_{OC}$ of approximately 11.7 volts. Capacitor banks 42G and 42H comprise, for example, ultracapacitors, such as PC100 ultracapacitors commercially available from Maxwell Technologies, Inc. Ultracapacitors, also called supercapacitors, are compact capacitors with high energy density.

Ultracapacitors can store more energy than conventional capacitors. To supply enough energy for a single defibrillation shock, second power pack 42 should store at least 100 joules. In the embodiment shown in FIG. 4, each ultracapacitor may store about 300 joules, and consequently, second power pack 42 may store enough energy for several defibrillation shocks. Furthermore, ultracapacitors can release the energy at a high rate or a low rate.

Ultracapacitors can be used as direct current power sources, like batteries. In addition, ultracapacitors are capable of delivering the high amperages demanded by charging circuit 26 to charge energy storage device 22 quickly. No special recharging apparatus is needed to recharge ultracapacitors.

The embodiments shown in FIGS. 3 and 4 are not exclusive. Power source 30 may comprise a combination of batteries and capacitors. In particular, second power pack 42 may include a combination of rechargeable batteries and rechargeable capacitors.

Figure 5:
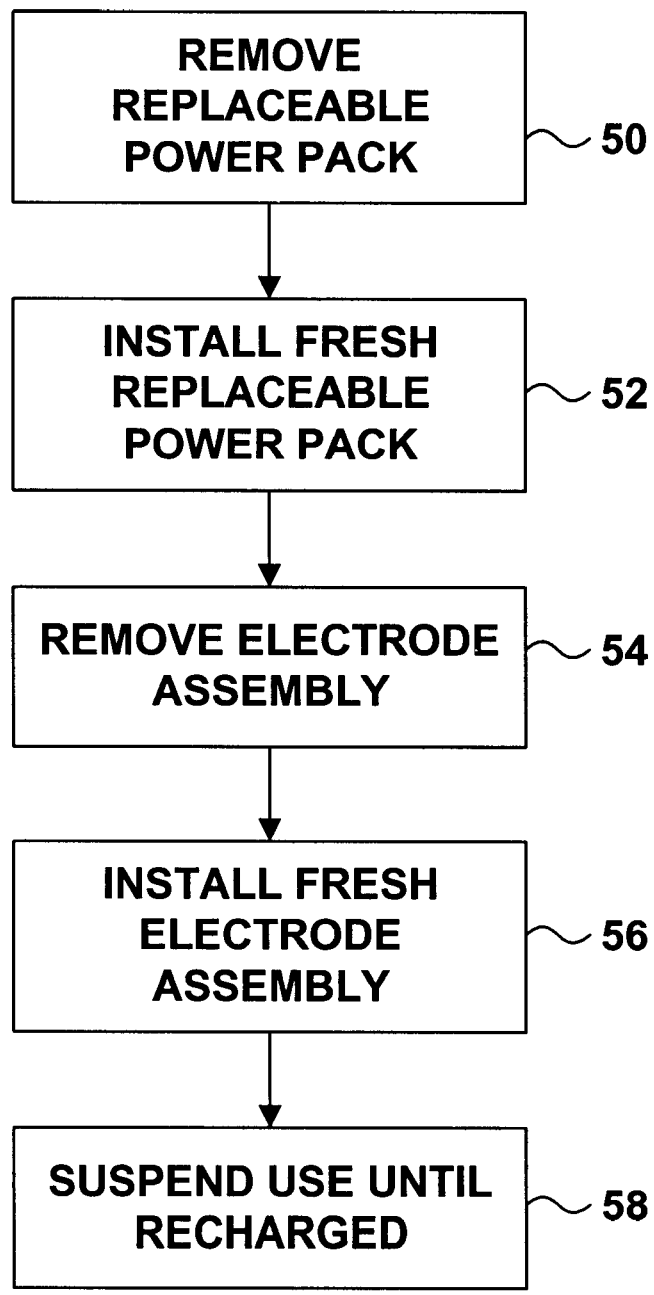
FIG. 5 is a flowchart illustrating techniques for maintaining a defibrillator that includes a replaceable first power pack and a rechargeable second power pack.

FIG. 5 is a flow diagram illustrating techniques for maintenance of a portable external defibrillator. A maintenance person uncouples first power pack 40 from second power pack 42 and removes first power pack 40 from compartment 34 (50). The maintenance person installs a fresh first power pack 40 (52) by inserting fresh first power pack 40 into compartment 34 and coupling fresh first power pack 40 to second power pack 42.

Although first power pack 40 and second power pack 42 have a low self-discharge rate and a long shelf life, first power pack 40 should ordinarily be replaced at regular intervals, even when defibrillator 18 is not used in the interim. As mentioned above, defibrillator 18 may include an I/O device 28, such as an LED indicator, that signals when it is time to replace first power pack 40. Furthermore, replacement of first power pack 40 is recommended after defibrillator 18 is used, because usage may have discharged second power pack 42.

For simplicity, it is easiest to replace first power pack 40 whenever electrodes 12 and 14 are replaced. In a typical portable defibrillator, electrodes 12 and 14 are single-use electrodes and are to be replaced after each use. Even if defibrillator 18 is not used, electrodes 12 and 14 are typically replaced after about two years. Electrodes 12 and 14 may include a substance such as hydrogel that hydrates the skin of patient 8, forms an interface with patient 8, enhances the capacity of electrodes 12 and 14 to sense electrocardiogram signals from patient 8, promotes adhesion of electrodes 12 and 14 to the skin and reduces the risk of burns to patient 8 when a defibrillation shock is applied. Although electrodes 12 and 14 are usually sealed inside a pouch, electrodes 12 and 14 are periodically replaced because the substance may dry out or otherwise degrade.

Accordingly, whenever electrodes 12 and 14 are removed (54) and replaced (56), it is sensible to replace first power pack 40 as well (50, 52). When first power pack 40 is installed, first power pack 40 recharges second power pack 42. Recharging may require time, however, so use of defibrillator 18 may be suspended (58) until second power pack 42 is recharged. Defibrillator may include an I/O device 28 that denotes recharge, such as an LED indicator that illuminates when second power pack 42 is recharged.

The time needed to recharge second power pack 42 depends on the extent to which second power pack 42 has discharged. Use of defibrillator 18 will not, in many cases, fully discharge second power pack 42. Furthermore, when first power pack 40 is replaced after two years as a part of scheduled maintenance, the discharge of second power pack 42 may be negligible.

The invention offers several advantages. Replaceable first power pack 40 and rechargeable second power pack 42 in power source 30 cooperate to provide the power needed by charging circuit 26 and energy storage device 22. No line power is needed, and consequently the electrical isolation circuitry needed for a line-powered defibrillator is not present. In addition, first power pack 40 recharges second power pack 42 without the need for a special charging device. When first power pack 40 supplies low currents, first power pack 40 recharges second power pack 42 without the need for heavy-duty connectors. As a result, defibrillator 18 is small, light and portable.

There are additional advantages to using lithium thionyl chloride batteries in replaceable first power pack 40 and lithium ion batteries in rechargeable second power pack 42. The batteries can have matched working voltages. The batteries operate over a wide temperature range. Both kinds of batteries are very small and light, which help make defibrillator 18 small, light and portable. The batteries have a very long shelf life. In addition, neither battery vents harmful electrolytes in case of failure.

Various embodiments of the invention have been described. These embodiments are illustrative of the practice of the invention. Various modifications may be made without departing from the scope of the claims. For example, the invention is not limited to the configurations of batteries and/or capacitors described herein. For example, individual batteries within power packs 40, 42 may be coupled in a variety of series and/or parallel connections, and power packs 40, 42 may be coupled to each other in different ways.

Nor is the invention limited to use of lithium thionyl chloride batteries in replaceable first power pack 40 and lithium ion batteries in rechargeable second power pack 42. Other batteries may be used as replaceable or rechargeable batteries. These and other embodiments are within the scope of the following claims.

We claim:

1. A defibrillator comprising a replaceable first battery coupled to a rechargeable second battery, wherein the rechargeable second battery is mounted permanently inside the defibrillator.

2. A defibrillator comprising a replaceable first battery coupled to a rechargeable second battery, further comprising an energy storage device that receives energy from the rechargeable second battery.

3. The defibrillator of claim 2, wherein the energy storage device comprises a capacitor.

4. The defibrillator of claim 2, further comprising a charging circuit that transfers energy from the rechargeable second battery to the energy storage device.

5. The defibrillator of claim 1, wherein the replaceable first battery comprises a lithium thionyl chloride battery.

6. The defibrillator of claim 1, wherein the replaceable first battery comprises a fuel cell.

7. The defibrillator of claim 1, wherein the rechargeable second battery comprises a lithium ion battery.

8. The defibrillator of claim 1, further comprising a battery compartment that receives the replaceable first battery.

9. The defibrillator of claim 8, the battery compartment comprising an electrical connection that couples the replaceable first battery to the rechargeable second battery.

10. The defibrillator of claim 1, wherein the replaceable first battery and the rechargeable second battery are coupled in parallel.

11. The defibrillator of claim 2, wherein the replaceable first battery comprises a lithium thionyl chloride battery.

12. The defibrillator of claim 2, wherein the replaceable first battery comprises a fuel cell.

13. The defibrillator of claim 2, wherein the rechargeable second battery comprises a lithium ion battery.

14. The defibrillator of claim 2, further comprising a battery compartment that receives the replaceable first battery.

15. The defibrillator of claim 14, the battery compartment comprising an electrical connection that couples the replaceable first battery to the rechargeable second battery.

16. The defibrillator of claim 2, wherein the replaceable first battery and the rechargeable second battery are coupled in parallel.

17. The defibrillator of claim 2, wherein the rechargeable second battery is mounted permanently inside the defibrillator.

* * * * *

UNITED STATES PATENT AND TRADEMARK OFFICE
CERTIFICATE OF CORRECTION

PATENT NO.    : 6,639,381 B2
DATED         : October 28, 2003
INVENTOR(S)   : Tamura et al.

It is certified that error appears in the above-identified patent and that said Letters Patent is hereby corrected as shown below:

Column 7,
Line 17, "power necks" should read -- power packs --

Signed and Sealed this

Twenty-sixth Day of October, 2004

JON W. DUDAS
*Director of the United States Patent and Trademark Office*